United States Patent
Case et al.

(10) Patent No.: US 10,413,653 B2
(45) Date of Patent: Sep. 17, 2019

(54) FLUID PROCESSING CASSETTE AND SENSOR COUPLING SYSTEM AND METHOD

(71) Applicant: Fenwal, Inc., Lake Zurich, IL (US)

(72) Inventors: Brian C. Case, Lake Villa, IL (US); Richard L. West, Lake Villa, IL (US); Randy K. Murphey, Pleasant Prairie, WI (US); Christopher J. Bishof, Palatine, IL (US)

(73) Assignee: Fenwal, Inc., Lake Zurich, IL (US)

( * ) Notice: Subject to any disclaimer, the term of this patent is extended or adjusted under 35 U.S.C. 154(b) by 297 days.

(21) Appl. No.: 15/472,546

(22) Filed: Mar. 29, 2017

(65) Prior Publication Data
US 2017/0290972 A1 Oct. 12, 2017

Related U.S. Application Data

(60) Provisional application No. 62/320,160, filed on Apr. 8, 2016.

(51) Int. Cl.
*A61M 1/38* (2006.01)
*A61M 1/36* (2006.01)

(52) U.S. Cl.
CPC ........ *A61M 1/3639* (2013.01); *A61M 1/3693* (2013.01); *A61M 1/38* (2013.01); *A61M 2205/12* (2013.01); *A61M 2205/121* (2013.01); *A61M 2205/128* (2013.01); *A61M 2205/3327* (2013.01); *A61M 2205/3331* (2013.01); *A61M 2209/084* (2013.01)

(58) Field of Classification Search
CPC ................ A61M 1/38; A61M 2205/12; A61M 2205/128; A61M 2205/3327; A61M 2205/3331; A61M 2205/121; A61M 1/3693
See application file for complete search history.

(56) References Cited

U.S. PATENT DOCUMENTS

| 4,798,090 A | 1/1989 | Heath et al. |
| 5,868,696 A | 2/1999 | Giesler et al. |
| 8,758,288 B2 | 6/2014 | Manzella, Jr. et al. |

FOREIGN PATENT DOCUMENTS

| WO | 1999011305 A1 | 3/1999 |
| WO | 2014099779 A1 | 6/2014 |

OTHER PUBLICATIONS

Extended European Search Report for application No. 17164995.7, dated Aug. 29, 2017, 6 pages.

*Primary Examiner* — Leslie R Deak
(74) *Attorney, Agent, or Firm* — Cook Alex Ltd.

(57) ABSTRACT

A fluid processing cassette and sensor coupling system is disclosed, comprising a cassette comprising a cap having an opening formed by an inner cylindrical wall having a first diameter, an outer cylindrical wall having a second diameter, and a contact surface connecting the inner and outer cylindrical walls. The contact surface includes a varying diameter that decreases from the second diameter to the first diameter. A sensor post comprises a ring disposed around a cylindrical body and is positioned to engage with the contact surface of the cap to form a seal.

13 Claims, 15 Drawing Sheets

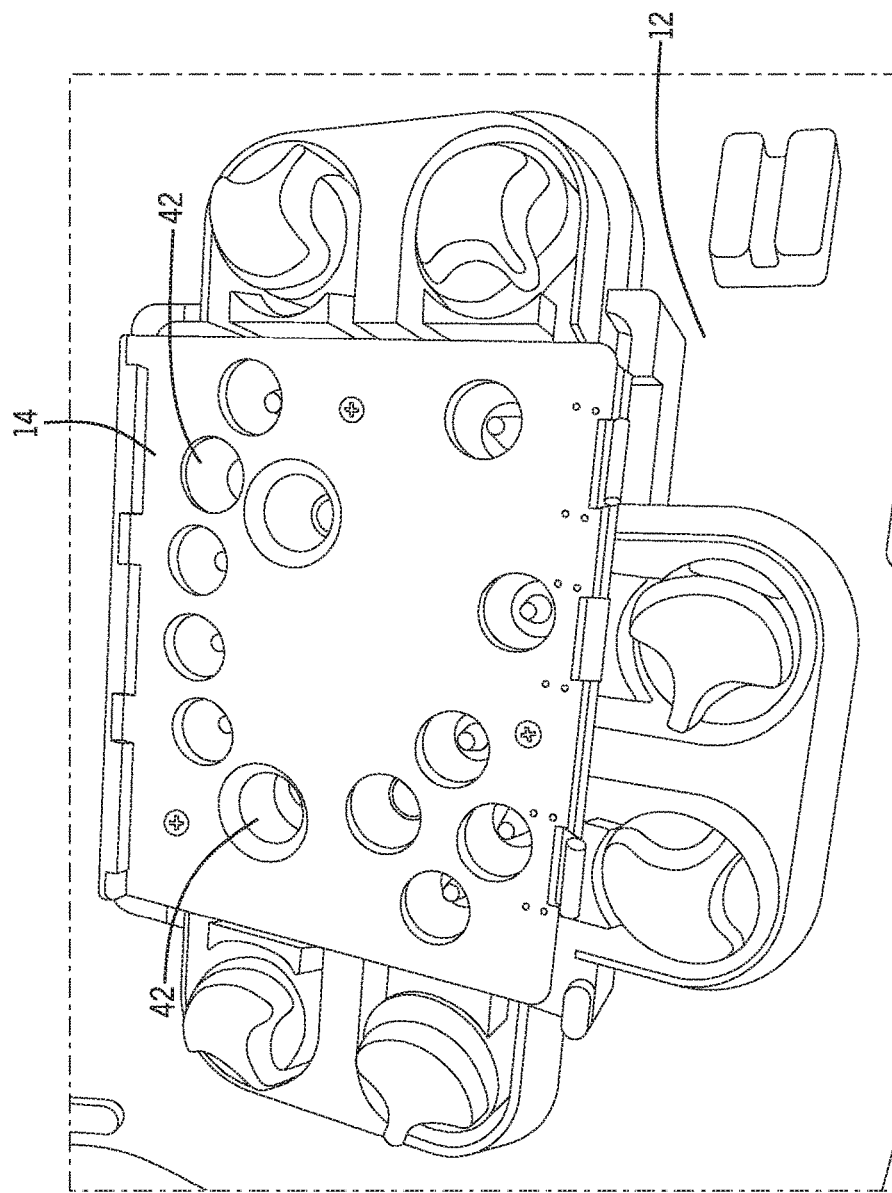

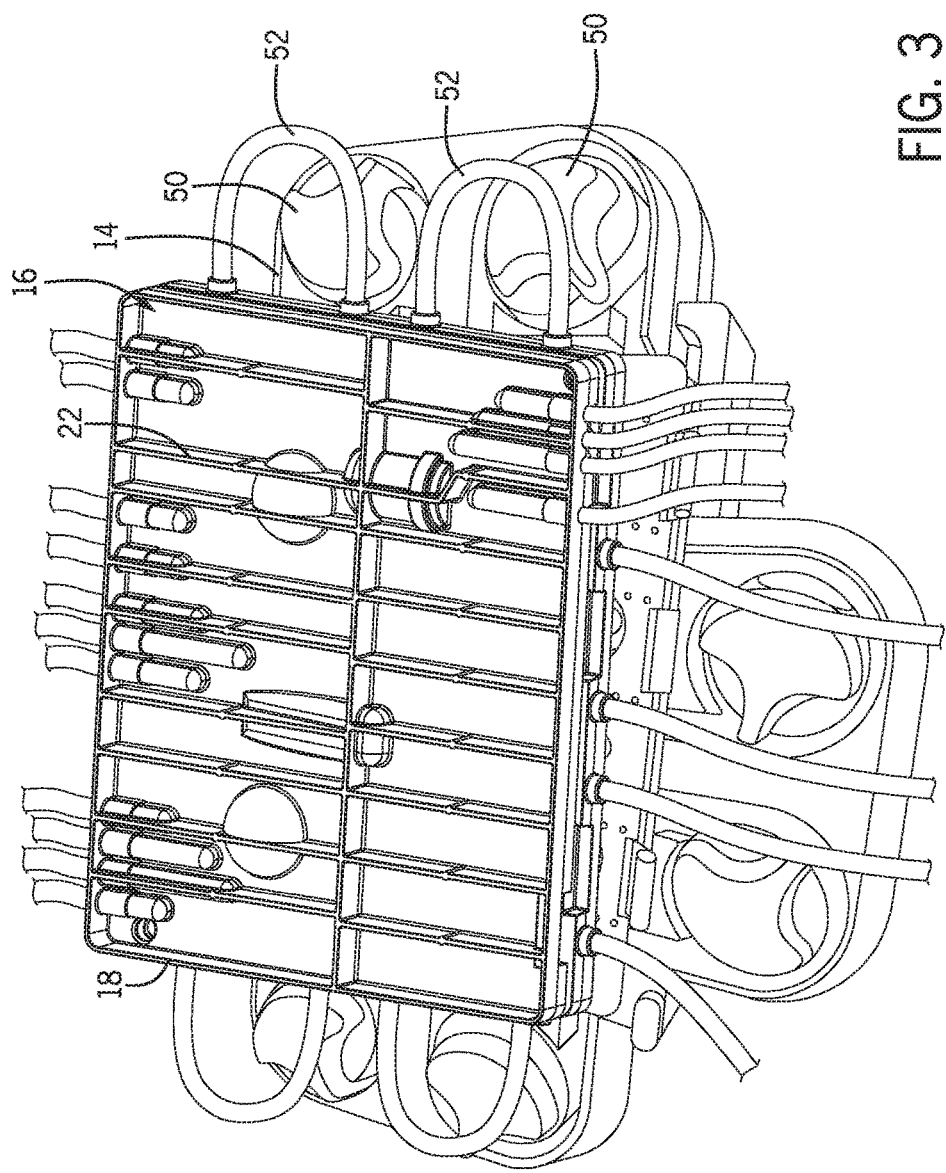

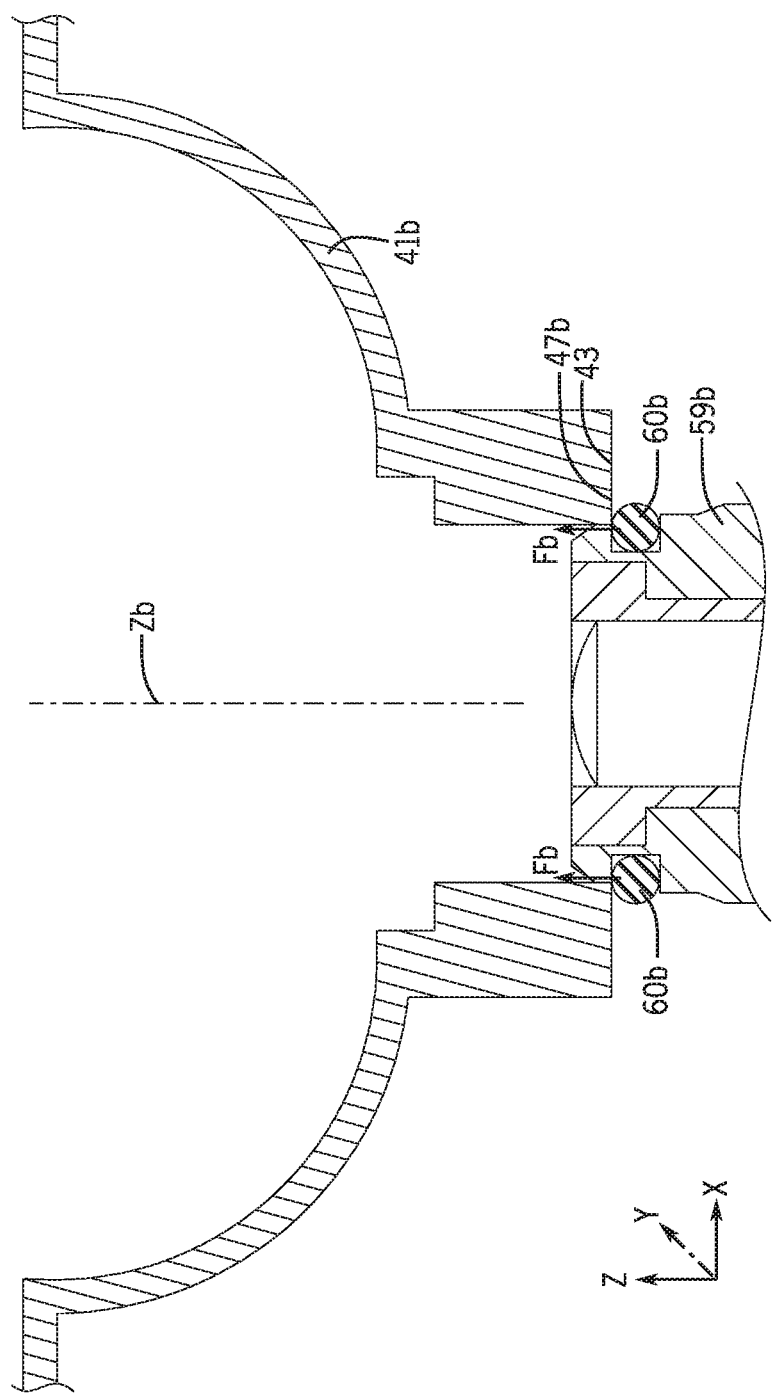

FLUID PROCESSING CASSETTE AND SENSOR COUPLING SYSTEM AND METHOD

CROSS-REFERENCE TO RELATED APPLICATIONS

This application claims the benefit of U.S. Provisional Patent App. No. 62/320,160 filed Apr. 8, 2016, which is expressly incorporated herein by reference in its entirety.

FIELD OF THE DISCLOSURE

The present disclosure relates to coupling systems. More specifically, the present disclosure relates to systems and methods for coupling fluid processing disposable cassettes to pressure sensing hardware.

BACKGROUND

Whole blood may routinely be separated into its various components, such as red blood cells, platelets, and plasma. Conventional blood processing methods may use durable separator equipment (e.g., centrifuge, spinning membrane) in association with single use, sterile processing sets, typically made of plastic. The configuration of the single use processing sets used in combination with different separator equipment may vary widely, but some sets may include a molded plastic piece commonly referred to as a cassette. As used herein, the term "cassette" refers to a component of a blood processing system which includes a number of defined fluid passageways and valve stations. The cassette is commonly secured to a cassette holder of the durable equipment via motor-powered grippers or mechanical latches. The cassette holder may include actuators for opening and closing the valve stations, which determine which of the fluid passageways are connected to each other, thereby directing fluid between a number of sources and destinations.

SUMMARY

According to an exemplary embodiment, the present disclosure is directed to a fluid processing system comprising a cassette comprising a molded body having a plurality of valve stations and at least one pressure sensing station, wherein the pressure sensing station comprises a cap having an opening extending beyond the molded body. The fluid processing system also comprises a loading area configured to receive and hold the cassette, and configured to position the cassette onto a valve and sensor assembly, wherein the valve and sensor assembly comprises valve actuators and at least one pressure sensing transducer comprising a sensor post, the valve and sensor assembly configured to align respectively with the plurality of valve stations and the pressure sensing station. The opening of the cap is formed by an inner wall having a first diameter, an outer wall having a second diameter, and a contact surface connecting the inner and outer wall. The contact surface includes a varying diameter that decreases from the second diameter to the first diameter, and the sensor post comprises a ring disposed around a cylindrical body and positioned to engage with the contact surface of the cap to form a seal.

According to an exemplary embodiment, the present disclosure is directed to a fluid processing cassette and sensor coupling system comprising a cassette comprising a cap having an opening formed by an inner cylindrical wall having a first diameter, an outer cylindrical wall having a second diameter, and a contact surface connecting the inner and outer cylindrical walls. The contact surface includes a varying diameter that decreases from the second diameter to the first diameter. A sensor post comprises a ring disposed around a cylindrical body and is positioned to engage with the contact surface of the cap to form a seal.

According to an exemplary embodiment, the present disclosure is directed to a fluid processing cassette and sensor coupling system comprising a cassette comprising a cap having an opening formed by an inner cylindrical wall having a first diameter, an outer cylindrical wall having a second diameter, and a contact surface connecting the inner and outer cylindrical walls. The contact surface includes a varying diameter that decreases from the second diameter to the first diameter. The system also comprises a sensor post comprising a ring disposed around a cylindrical body and positioned to engage with the contact surface of the cap to form a seal, a bottom lip configured to contact and support the ring, a top lip, and a shim disposed between the ring and the bottom lip.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

FIG. 2 is a perspective view of a loading area of the system of FIG. 1, according to an exemplary embodiment;

FIG. 3 is a perspective view of a cassette prior to being loaded onto the loading area of FIG. 2, according to an exemplary embodiment;

FIG. 7C a cross-sectional diagram showing a sensor post forming a face seal with a cap of a cassette sensing station, according to an exemplary embodiment;

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may facilitate measuring draw and return pressures from a donor/patient without blood being in direct contact with a pressure sensor.

Some embodiments may enable measuring pressure in multiple locations within a fluid transport system, e.g., a cassette.

Some embodiments may enable alignment of multiple couplings, thereby accommodating larger manufacturing variations.

An exemplary blood processing system as well as its cassette and cassette holder are described in greater detail in U.S. Pat. No. 5,868,696, which is hereby incorporated herein by reference in its entirety. In blood processing systems, fluid flow may be controlled by a disposable cassette with preformed fluid passages, which may interface with an array of actuators and sensors located on a panel of a durable reusable hardware. The cassette may have a flexible membrane on the side facing the actuators and sensors. A vacuum may be applied by the hardware through small spaced-apart apertures to draw the membrane into contact with the surface of the array and with the sensors therein for more reliable and accurate sensing. Specifically, a thin, elastomeric membrane may be associated with the cassette holder and cover all of the actuators, The gasket may protect the actuators from liquids, dust, and other debris that could otherwise interfere with the performance of the actuators.

Figure 1:
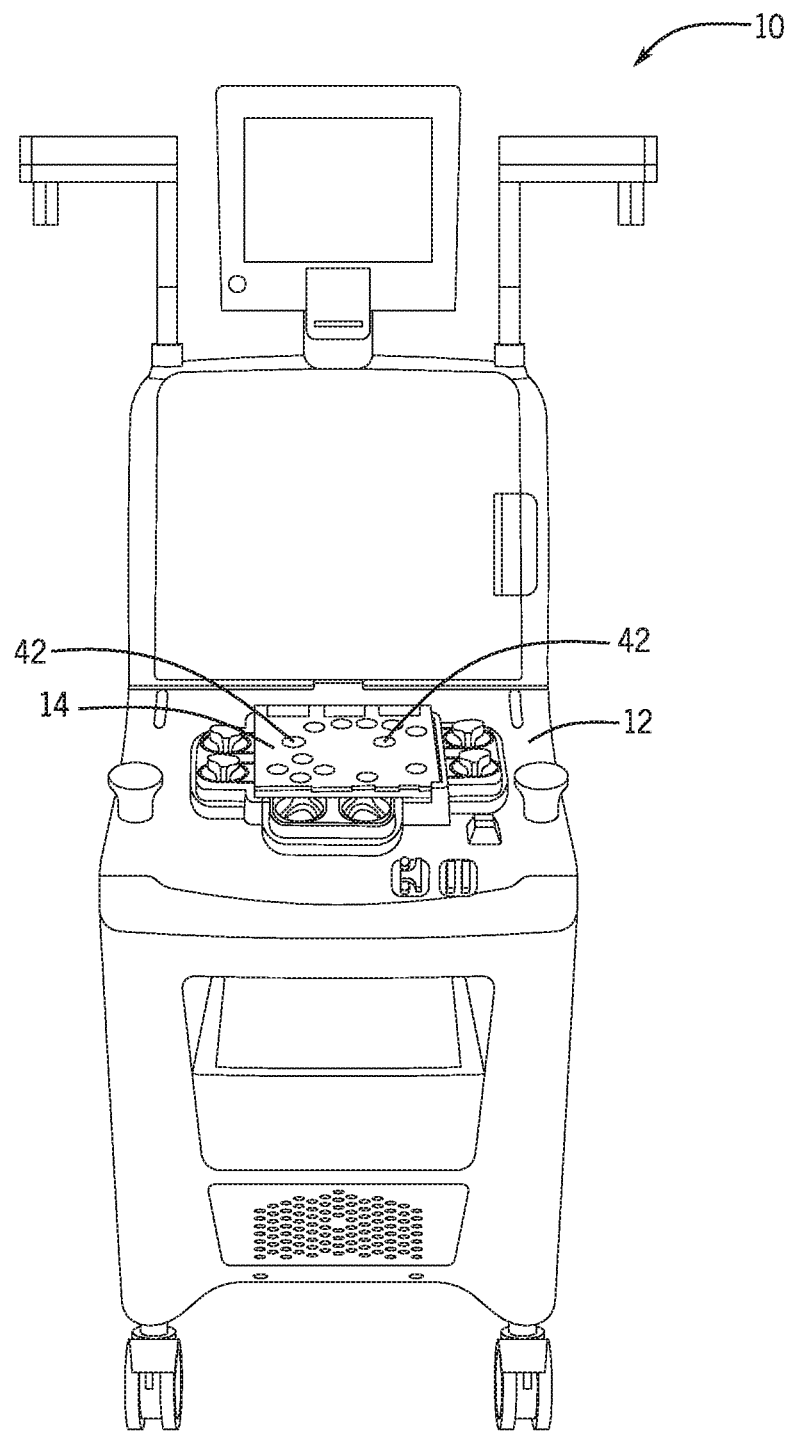
FIG. 1 is a front view of a fluid processing system for processing various fluids, according to an exemplary embodiment.

FIG. 1 shows a fluid processing system 10 that can be used for processing various fluids, but may be particularly well suited for processing whole blood and other suspensions of biological cellular materials. The system 10 may include a centrifuge or spinning membrane (not visible) suitable for separating a fluid into its components based on the density and/or size of such components.

Referring to FIG. 2, a sloped front panel 12 of the system 10 may include at least one loading area, such as cassette holder 14, which may be configured to receive and grip a cassette 16 (FIGS. 3 and 4) of a disposable, single-use processing set.

Figure 3A:
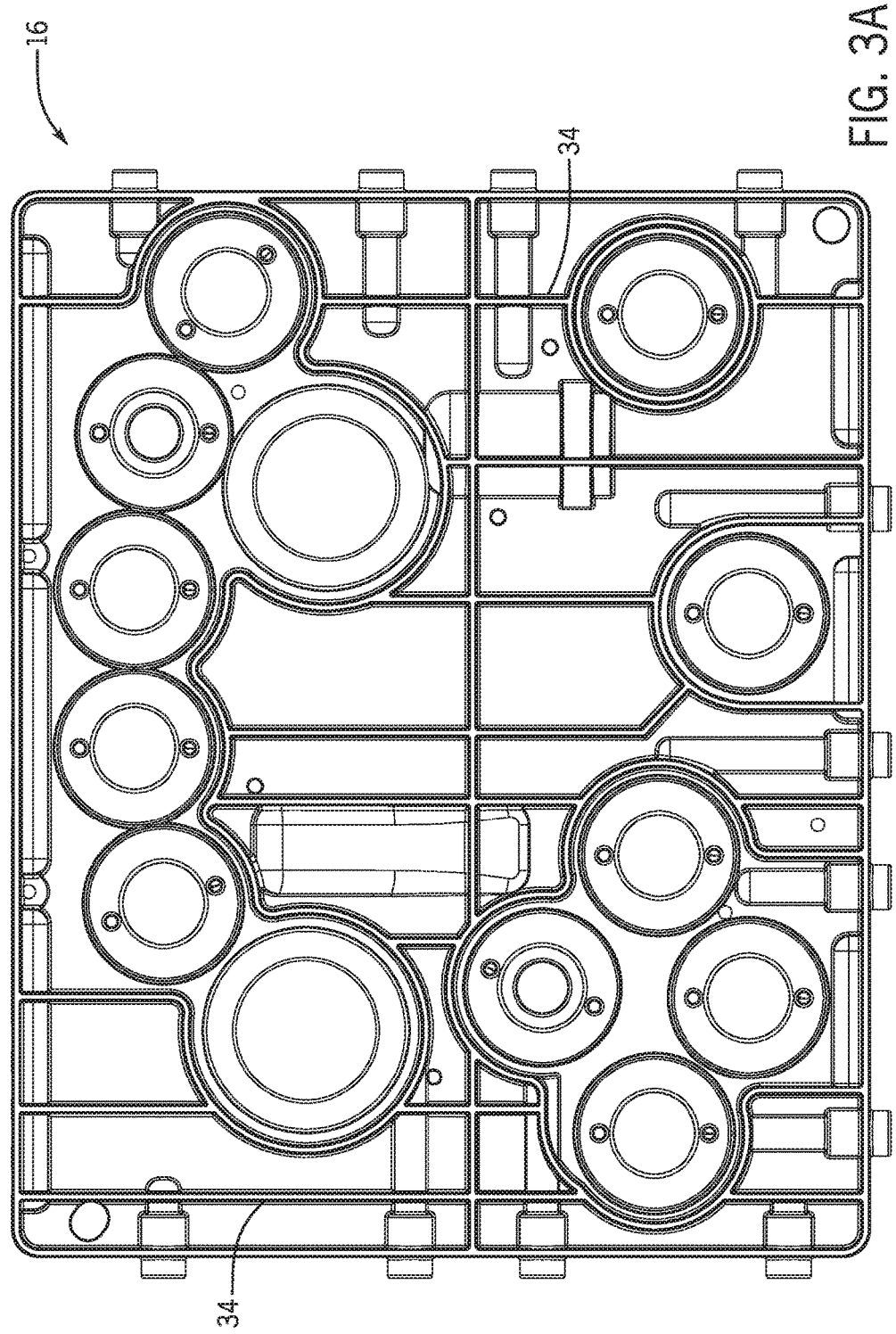
FIG. 3A is a diagrammatic view of the defined pathways of a cassette, according to an exemplary embodiment.
Figure 4:
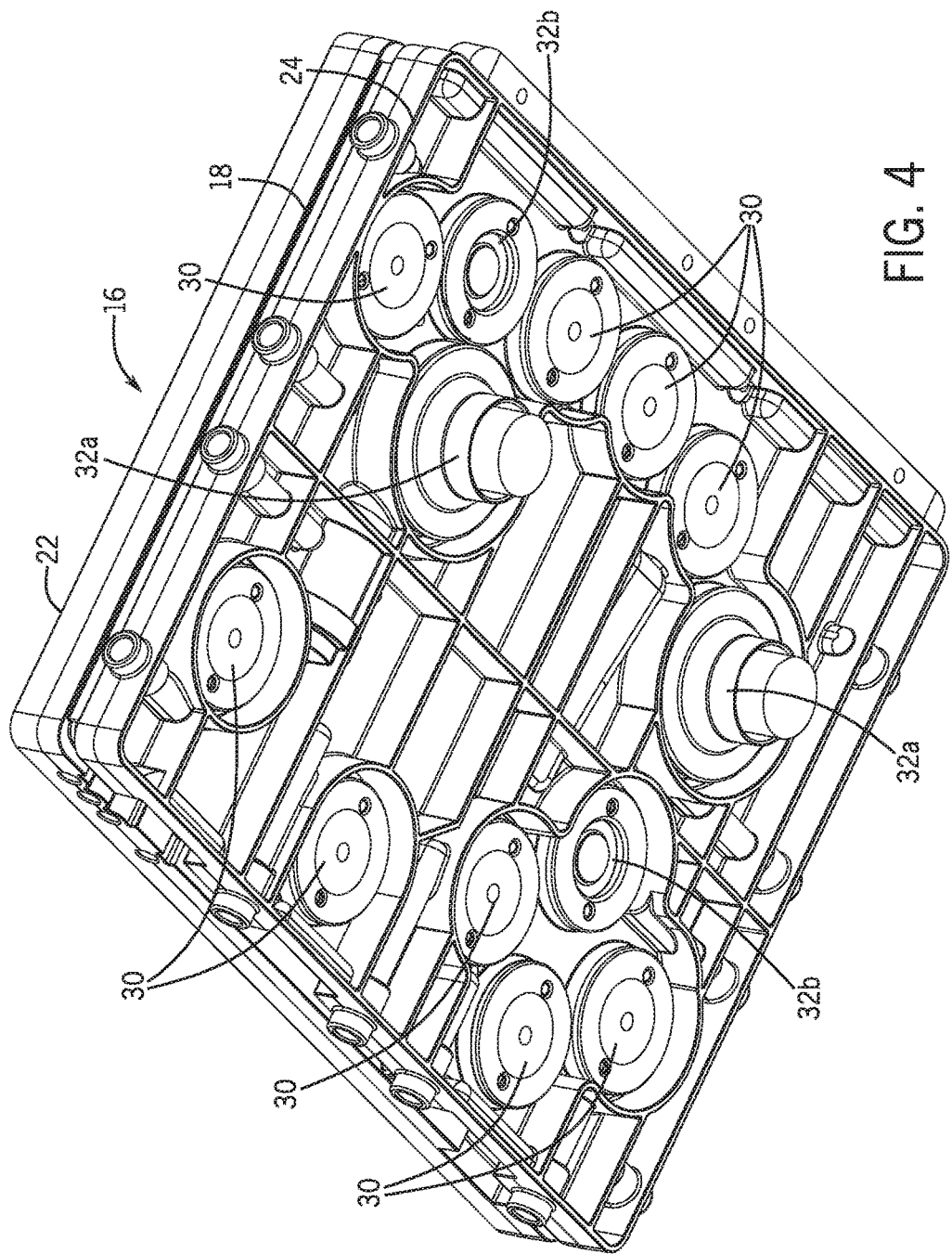
FIG. 4 is a perspective view of the bottom of a cassette, according to an exemplary embodiment.

The cassette 16, as shown in FIGS. 3, 3A, and 4, may include an injection molded body 18 that may be compartmentalized to form defined pathways, e.g., pathways 34 in FIG. 3A. The body 18 may be covered by a top cover 22 (FIG. 3) and a bottom cover 24 (FIG. 4), enabling the cassette and its fluid contents to be closed from the surrounding environment. For the purposes of description, the top cover 22 is disposed on the side of the cassette 16 that, in use, faces away from the system 10, while the bottom cover 24 faces towards the system 10. A flexible diaphragm 26 (not shown) may be disposed between the bottom cover 24 and the body 18, thereby sealing the underside of the body 18 from the system 10 and cassette holder 14. In one embodiment, the cassette 16, the cassette body 18, the top cover 22, and/or the bottom cover 24 may be made of a rigid medical grade plastic material, while the diaphragm 26 may be made of a flexible sheet of medical grade plastic.

As shown in FIG. 4, the bottom cover 24 may include an array of valve stations 30 disposed under select locations of the various defined pathways of the body 18. The bottom cover 24 may also include pressure sensing stations 32a and 32b. The valve stations 30 and the pressure sensing stations 32a and 32b may communicate with the various defined pathways in a predetermined manner. The number and arrangement of the valve stations 30, and the sensing stations 32a and 32b may vary.

Turning to FIGS. 2 and 3, the cassette holder 14 may be configured to receive and grip the cassette 16 in a desired operating position. The cassette holder 14 may include any number of peristaltic pump stations 50. When the cassette 16 is loaded, tubing loops 52 extending from the cassette 16 may make operative engagement with the pump stations 50. The pump stations 50 may be operated to cause fluid flow through the cassette 16.

Turning to FIGS. 2 and 3, the cassette holder 14 may be configured to receive and grip the cassette 16 in a desired operating position. The cassette holder 14 may include any number of peristaltic pump stations 50. When the cassette 16 is loaded, tubing loops 52 extending from the cassette 16 may make operative engagement with the pump stations 50. The pump stations 50 may be operated to cause fluid flow through the cassette 16.

Figure 5:
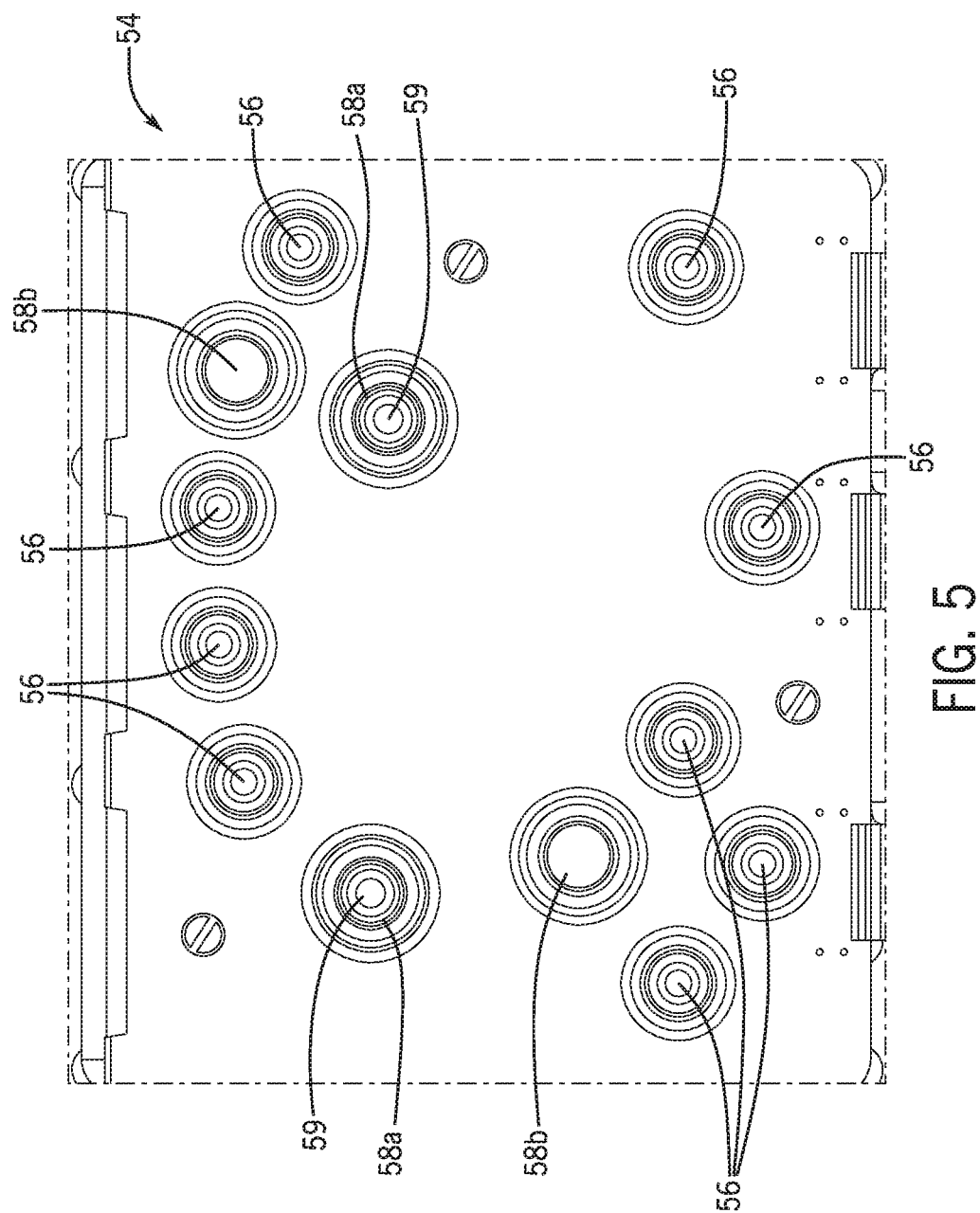
FIG. 5 is a top view of a valve and sensor assembly of a cassette, according to an exemplary embodiment.

When the cassette 16 is loaded onto the cassette holder 14, the blood processing system 10 may be configured to lower the cassette holder into contact with a valve and sensor assembly 54, illustrated in FIG. 5, located underneath the cassette holder 14 within the blood processing system 10. The cassette holder 14 may include a plurality of openings 42 to allow components of the valve and sensor assembly 54 to access the valve stations 30 and sensing stations 32 of the cassette 16 when the cassette 16 and cassette holder 14 are lowered into contact with the valve and sensor assembly 54. FIG. 5 is a top view of one embodiment of a valve and sensor assembly 54. The valve and sensor assembly 54 may act in concert with the valve stations 30 and sensing stations 32a and 32b of the cassette 16 to control and monitor fluid flow within the cassette 16. The valve and sensor assembly 54 may include valve actuators 56 and pressure sensing transducers 58a and 58b. The valve actuators 56 and the pressure sensing transducers 58a and 58b may be mutually arranged in the same layout as the valve stations 30 and sensing stations 32a and 32b on the underside 24 of the cassette 16.

When the cassette 16 is gripped by the cassette holder 14, the valve actuators 56 may align with the cassette valve stations 30. At the same time, the pressure sensing transducers 58a and 58b may mutually align with the pressure sensing stations 32a and 32b, respectively. The pressure sensing transducers 58a and 58b may utilize a piezoelectric mechanism and comprise a sensor post, although any suitable pressure sensing mechanism may be used. Other pressure sensing mechanisms include bridge-based, capacitive, and/or optical mechanisms. An exemplary valve/sensor assembly, cassette, and cassette holder are described in greater detail in U.S. Pat. No. 8,758,288, which is hereby incorporated herein by reference in its entirety.

Figure 6:
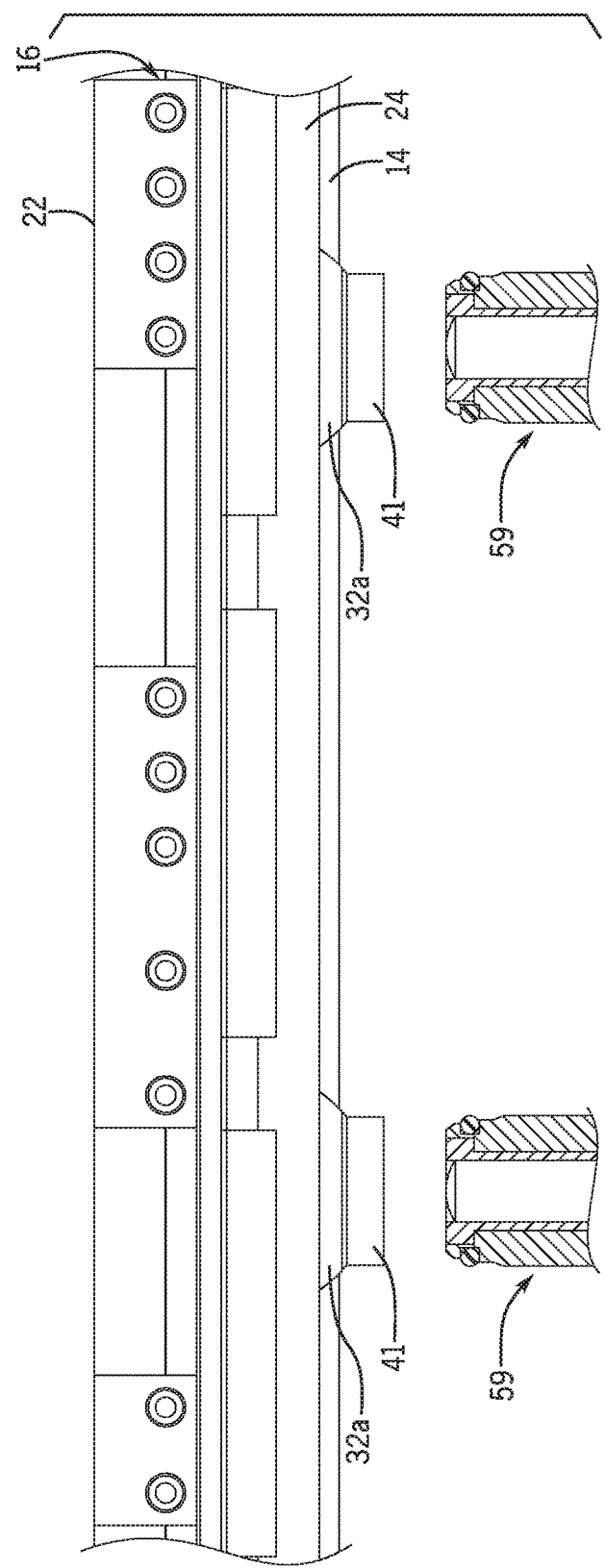
FIG. 6 is a cross-section elevational view of a cassette prior to engagement with a valve and sensor assembly, according to an exemplary embodiment.

FIG. 6 shows an elevational view of the cassette 16 prior to engagement with sensor posts 59 that form a part of the pressure sensing transducers 58a, 58b, of the valve and sensor assembly 54. FIG. 6 depicts the cassette 16 seated onto the cassette holder 14. The pressure sensing stations 32*a* and 32*b* of the cassette 16 may include caps 41 extending from the cassette's underside 24. When the cassette 16 is seated onto the cassette holder 14, the caps 41 may extend beyond the plane of the cassette holder 14 via the openings 42 (FIG. 2) of the cassette holder 14. Cap 41 may be configured to engage sensor post 59, ensuring that an effective seal is created for proper pressure sensing at each pressure sensing station 32*a* or 32*b*.

Figure 7A:
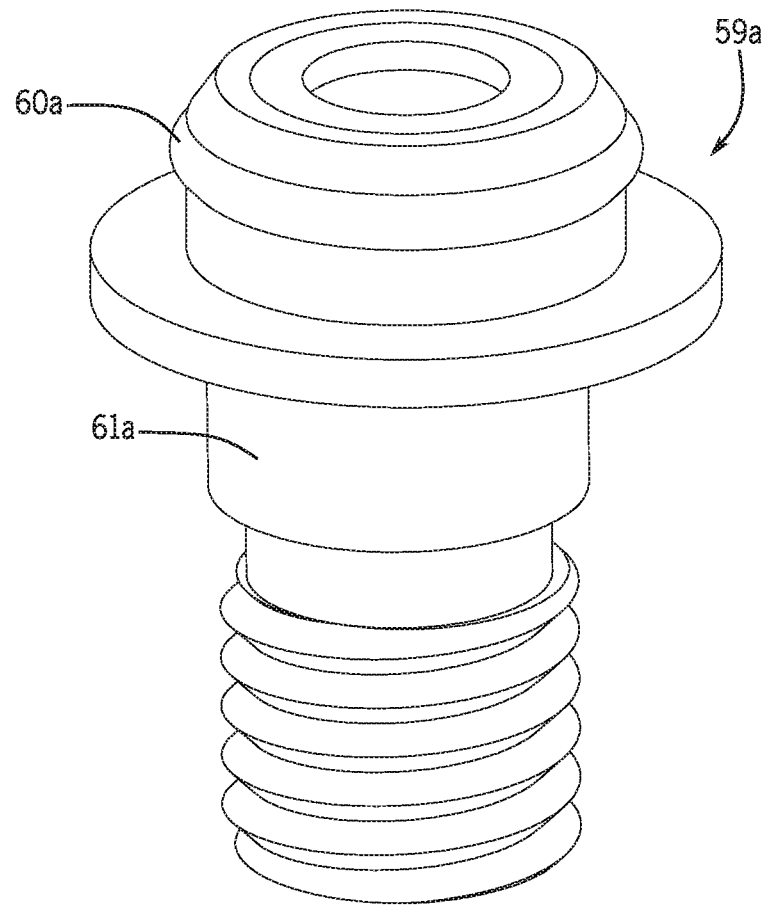
FIG. 7A is a perspective view of a sensor post known in the art, according to an exemplary embodiment.

FIG. 7A depicts a sensor post 59*a* known in the art. Sensor post 59*a* comprises a main cylindrical body 61*a* and a flexible ring 60*a*. Ring 60*a* is configured to tightly engage the circumference of the cylindrical body 61*a* to provide a tight seal.

Figure 7B:
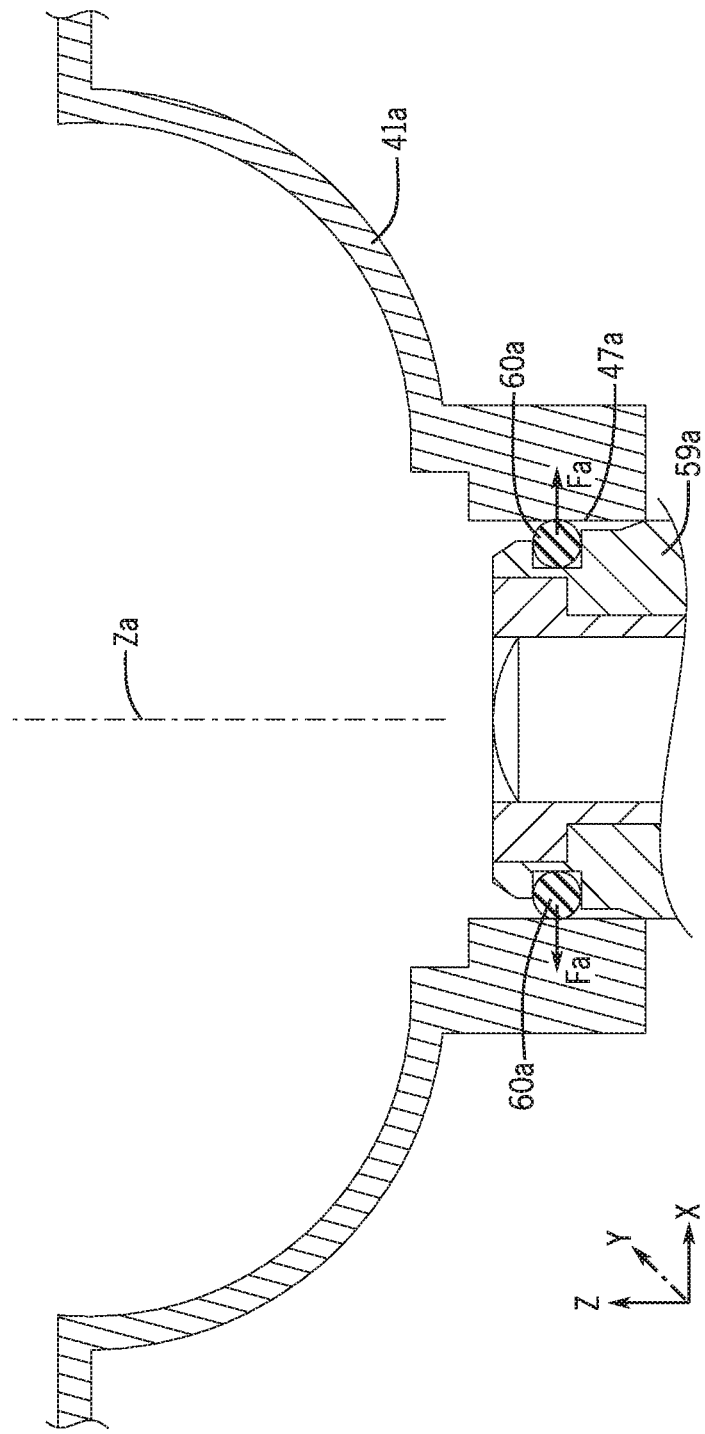
FIG. 7B is a cross-sectional diagram showing a sensor post of FIG. 7A forming a bore seal with a cap of a cassette sensing station, according to an exemplary embodiment.

FIG. 7B is a cross-sectional diagram showing sensor post 59*a* fitted within a cap 41*a* such that ring 60*a* is entirely within the cap 41*a* and the contact surface 47*a* is parallel to the axis Za of the seal. A seal is created by the ring 60*a* being tightly fitted within the cap 41*a* such that the ring 60*a* provides an effective barrier to fluid flow. The ring 60*a* exerts a force Fa against the cap 41*a* primarily in a radially outward direction perpendicular to the vertical wall of the cap 41*a* and perpendicular to the vertical axis Za of the seal. A seal such as that depicted in FIG. 7B is generally known in the art and is sometimes referred to as a bore seal.

FIG. 7C is a cross-sectional diagram showing sensor post 59*b* engaged with a cap 41*b* such that the contact surface 47*b* between the ring 60*b* and edge 43 is perpendicular to the axis Zb of the seal. A seal is created by the ring 60*b* making contact at a contact surface 47*b* having a horizontal component, disposed along the bottom edge 43 of the cap 41*b*. An effective seal is created by the ring 60*b* making contact with the contact surface 47*b* along a circumference of the bottom edge 43. The ring 60*b* exerts a force Fb against the bottom edge 43 primarily in a z-direction perpendicular to the horizontal contact surface 47*b* of the bottom edge 43 but parallel to the vertical axis Zb of the seal. A seal such as that depicted in FIG. 7C in which the contact surface between the ring 60*b* and edge 43 is perpendicular to the axis Zb is sometimes referred to as a face seal.

Referring to FIG. 6, in order for an effective seal to form between a sensor post 59 of and a cap 41 of the cassette 16, precise alignment of the sensor post 59 and cap 41 is oftentimes important. In the case of a bore seal, an effective seal may be more sensitive to precise alignment, as a bore seal requires a sensor post ring to fit entirely within the cap 41. A face seal may also be sensitive to precise alignment, as a shift in alignment in any x, y, z-direction may cause a sensor post ring to lose contact at a point along a circumference of the cap's bottom edge 43. Even after an effective seal is created, maintaining the seal is also important for accurate pressure sensing. Due to an exertion of force by the sensor post 59 onto the cap 41 as well as continuous impact forces exerted by the valve actuators 56 upwards onto the cassette 16 during a fluid processing procedure, the cassette 16 may incur deflection or distortion during the fluid processing procedure. Such deflection and/or distortion of the cassette 16 may lead to decoupling of the sensor post 59 to the cap 41, leading to a potential leak in the seal.

Figure 8A:
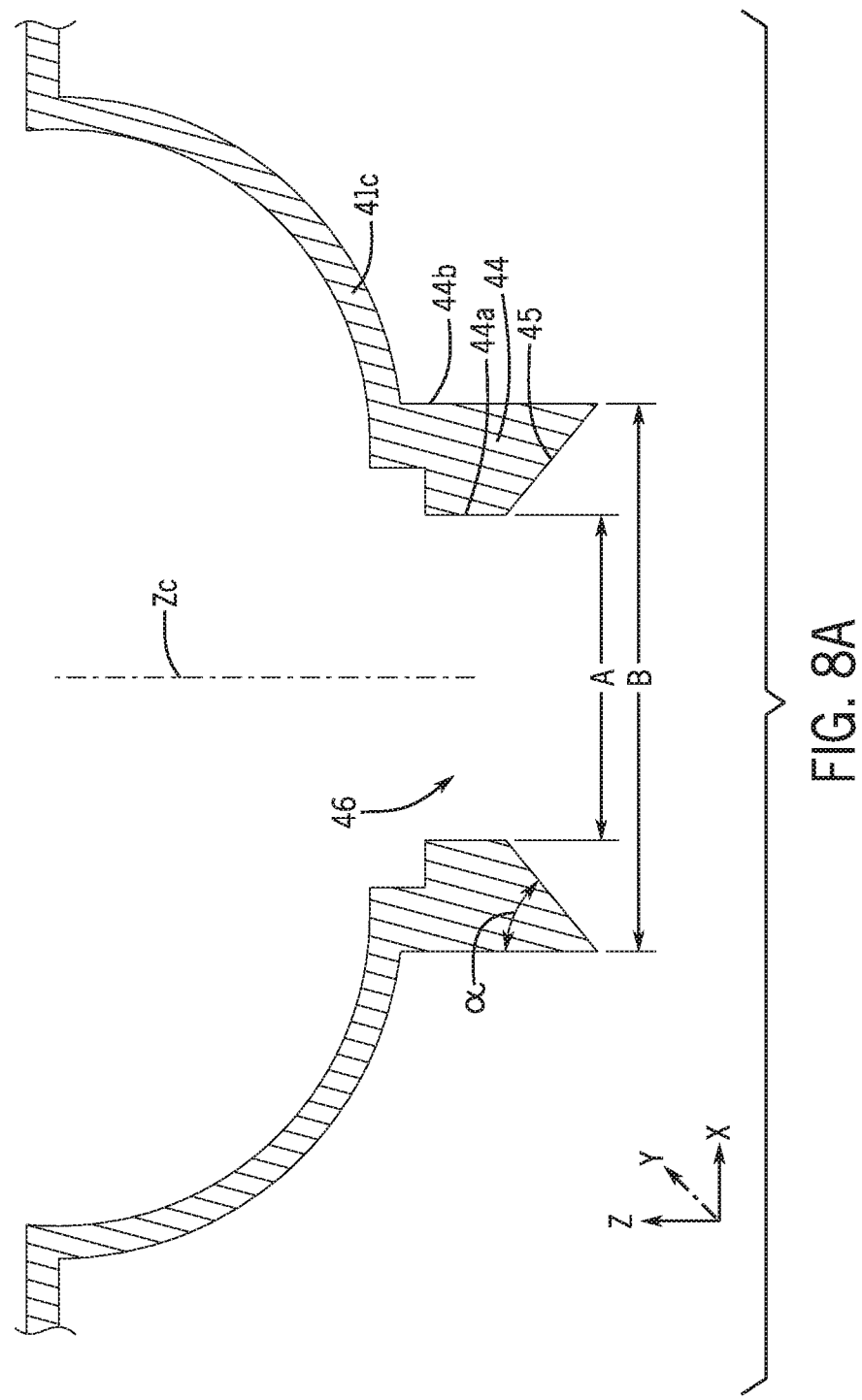
FIG. 8A is a cross-sectional diagram of a cap of a cassette sensing station, according to an exemplary embodiment.

Turning to FIG. 8A, a cross-sectional diagram of cap 41*c* according to an exemplary embodiment is shown. Cap 41*c* may comprise a cylindrical body 44 having an inner wall 44*a* having a diameter A and an outer wall 44*b* having a diameter B. A sloped wall 45 may connect the inner wall 44*a* to the outer wall 44*b*. The sloped wall 45 may form an opening 46 having a diameter that gradually decreases from B to A moving inwards further into the opening 46 of cap 41*c*. The sloped wall 45 may be disposed at an acute angle α relative to the vertical axis Zc of the seal. Angle α may have a value in the range of 30 to 60 degrees, preferably in the range of 40 to 50 degrees, and more preferably approximately 45 degrees. Angle α should preferably be large enough to maintain an effective seal even with minor shifts in the x-y (horizontal) direction between a sensor post and the cap 41*c*. The sloped wall 45 may comprise a surface finish, including, for example, SPI B-1. A higher (smoother) surface finish may be conducive to an effective seal, as a lower (rougher) surface finish may require a higher seal force to compress a ring into void areas of the cap 41*c* to prevent leakage.

Figure 8B:
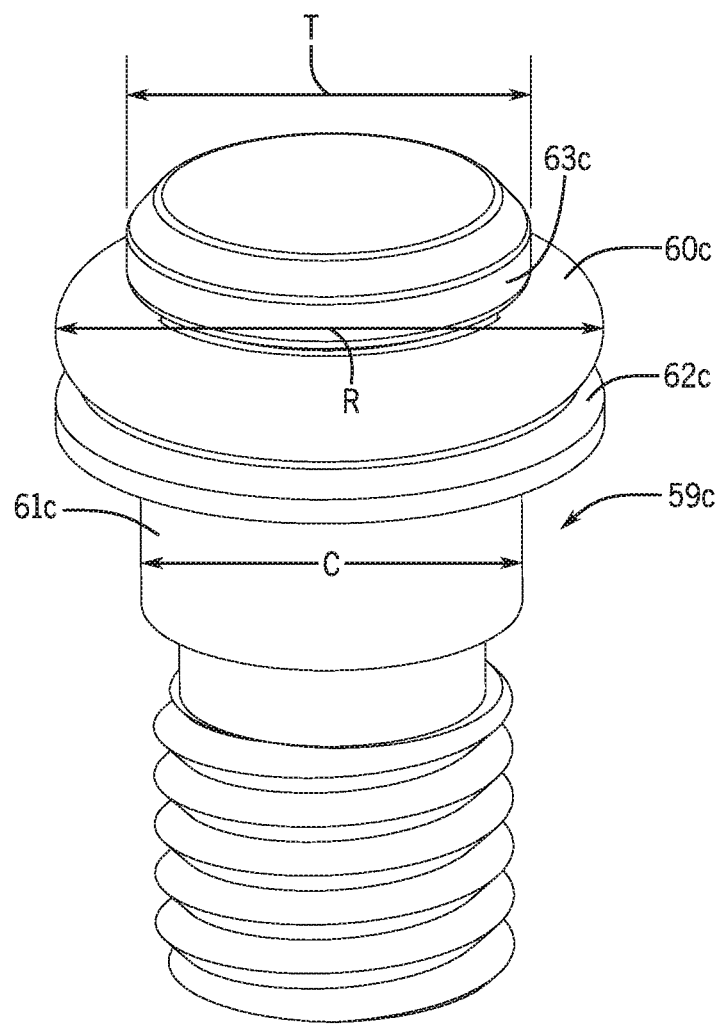
FIG. 8B is a perspective view of a sensor post, according to an exemplary embodiment.

FIG. 8B shows a sensor post 59*c* according to an exemplary embodiment. Sensor post 59*c* comprises a main cylindrical body 61*c* and a flexible ring 60*c*. Ring 60*c* is configured to tightly engage the circumference of the cylindrical body 61*c* to provide a tight seal. A bottom lip 62*c* may support the ring 60*c* and ensure that the ring 60*c* stays in place when the ring 60*c* is compressed against a cap of a cassette. A top lip 63*c* having a diameter T greater than the diameter C of the cylindrical body 61*c* may retain the ring 60*c* so that the ring 60*c* does not slide upwards off the sensor post 59*c*. Ring 60*c*, when engaged with the cylindrical body 61*c*, may have an outer diameter R. According to an exemplary embodiment, ring 60*c* may have a hardness value on the durometer scale in the range of 20 to 100 durometers, preferably in the range of 35 to 60 durometers, and more preferably approximately 40 durometers. The ring material may comprise one or more suitable materials, such as silicone, nitrile rubber, and/or a fluoropolymer elastomer, such as Viton.

Figure 8C:
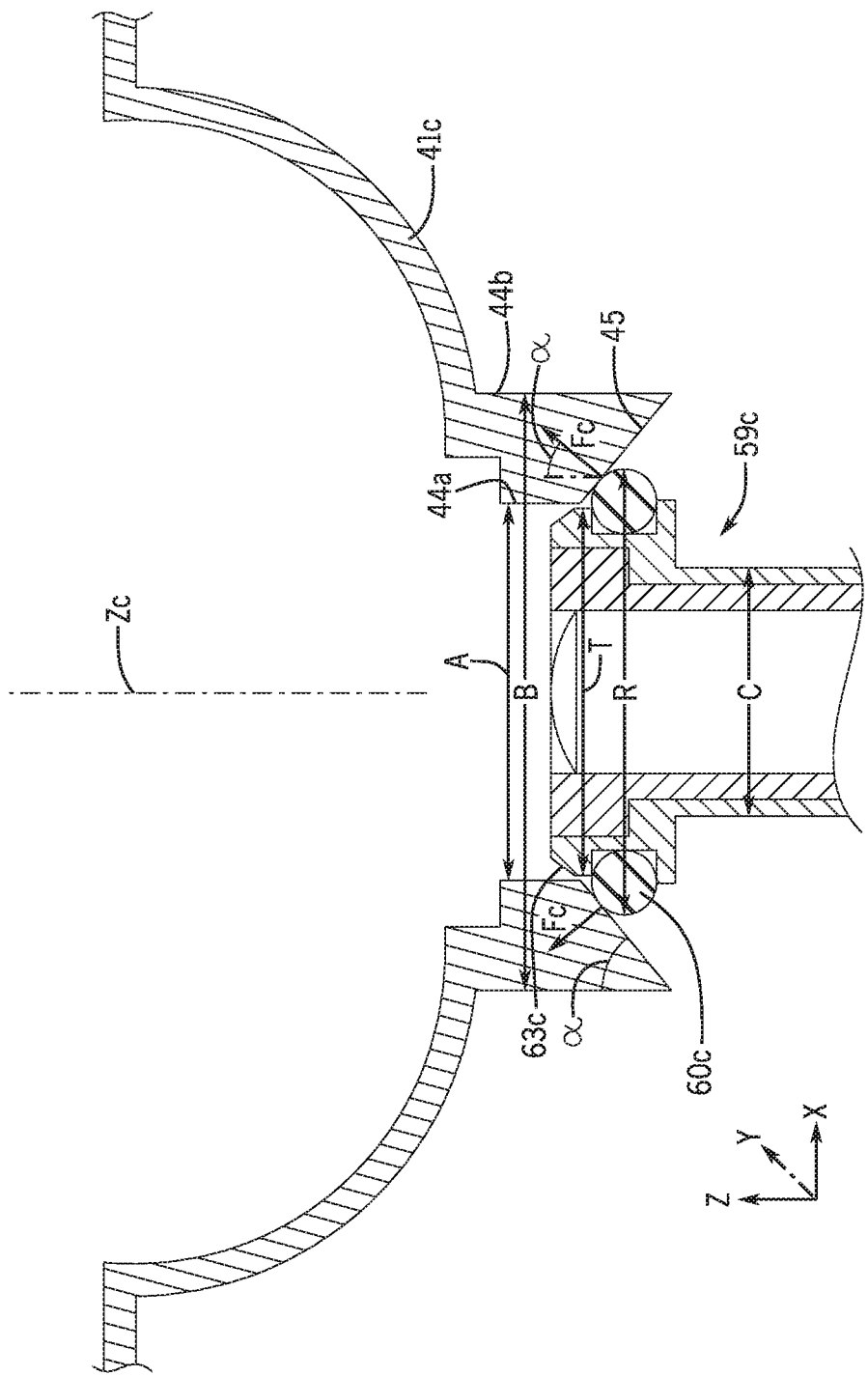
FIG. 8C is a cross-sectional diagram showing a sensor post forming a crush seal with a cap of a cassette sensing station, according to an exemplary embodiment.

FIG. 8C is a cross-sectional diagram showing a sensor post 59*c* fitted against the cap 41*c*. A seal is created by the ring 60*c* being fitted against the cap 41*c* such that the ring 60*c* provides an effective barrier to fluid flow. The ring 60*c* exerts a force Fc against the cap 41*c* perpendicular to the sloped wall 45 of the cap 41*c* and at angle α to the vertical axis Zc of the seal, the same angle as that which is formed between the sloped wall 45 and vertical axis Zc of the seal. A seal such as that depicted in FIG. 8C in which the ring 60*c* exerts a force Fc at an acute angle to the vertical axis Zc of the seal may be referred to herein as a crush seal. The crush seal described herein may be maintained without breaking due at least in part to its larger tolerance to movement and/or shifting between the cap 41*c* and sensor post 59*c* in any x, y, or z direction before an effective seal is lost.

In one embodiment, the inner wall 44*a* of the cap 41*c* may have a diameter A of at least 0.010 inches, preferably at least 0.250 inches, and more preferably approximately 0.281 inches. The outer wall 44*b* may have a diameter B greater than diameter A, preferably at least 0.030 inches greater than diameter A, and more preferably approximately 0.060 inches greater than diameter A. The difference in value of diameters A and B should be large enough to maintain robustness of the cap 41*c* to maintain its shape while in contact with the sensor post 59*c*. The top lip 63*c* of the sensor post 59*c* may have a diameter T having a value in the range of 1-25% less than diameter A and more preferably 5-10% less than diameter A. Diameter T of the top lip 63*c* should be a value low enough to prevent the top lip 63*c* from interfering with an effective seal. The outer diameter R of ring 60*c* may be a value greater than the value of diameter A and less than the value of diameter B. A ring having an R-value less than that of diameter A may not make contact with the cap 41*c* and not achieve an effective seal. A ring having an R-value greater than diameter B of the cap 41c may create a face seal instead of a crush seal.

Figure 9:
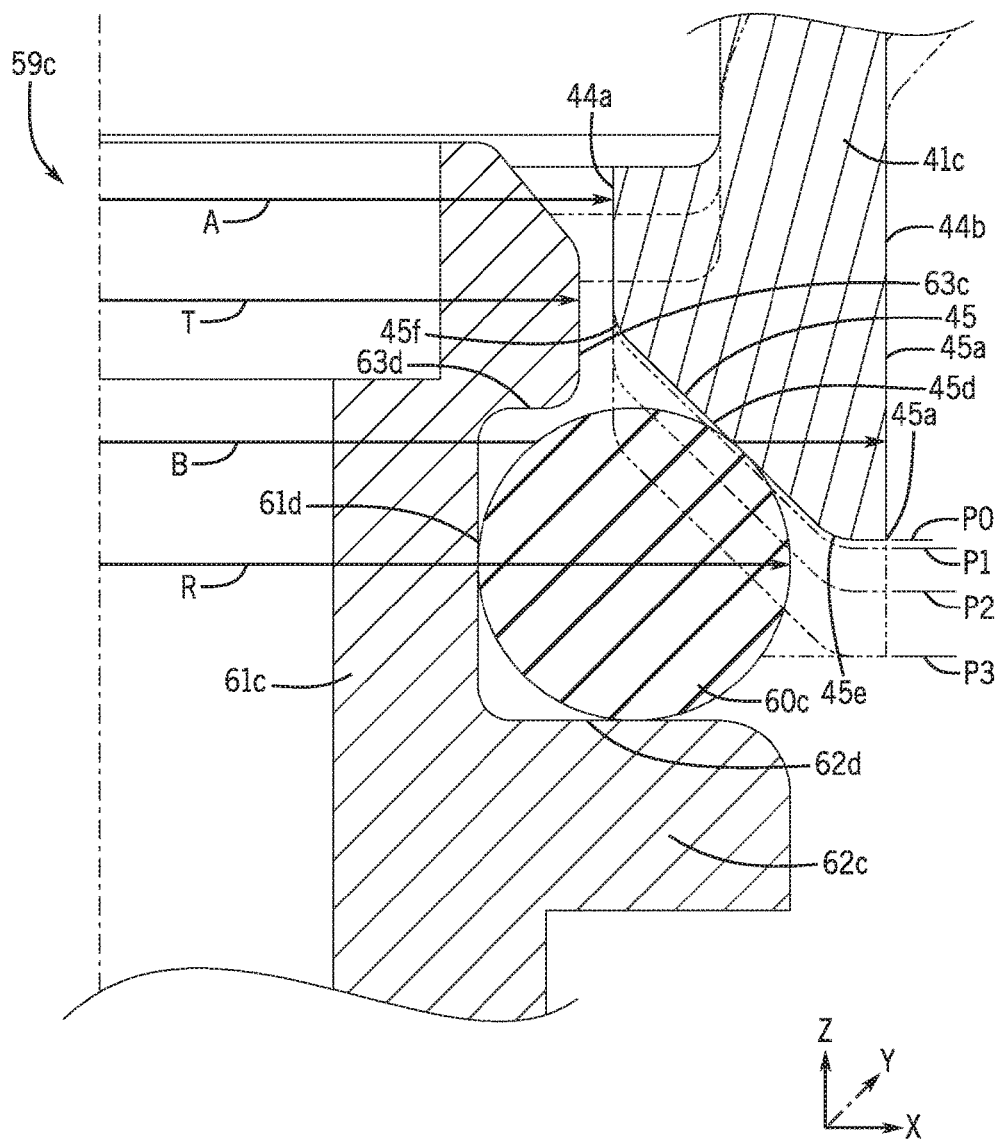
FIG. 9 is a cross-sectional diagram showing one side of a sensor post fitted against a cap of a cassette sensing station at different compression levels, according to an exemplary embodiment.

FIG. 9 is a cross-sectional diagram showing one side of a sensor post 59c fitted against the cap 41c at different compression levels, according to an exemplary embodiment. When the sensor post 59c is engaged with the cap 41c, ring 60c may be lodged between the cap 41c and the cylindrical body 61c of the sensor post 59c. The ring 60c may be positioned on the bottom lip 62c, making contact with a top surface 62d of the bottom lip 62c. The ring 60c, being tightly engaged with the cylindrical body 61c, may be compressed against a vertical surface 61d, along the length of the cylindrical body 61c, between the bottom lip 62c and the top lip 63c. The ring 60c may also make contact with the top lip 63c at a bottom surface 63d of the top lip 63c. An outer portion of the ring 60c may make contact with and/or be compressed by a contact surface 45d along the sloped wall 45 of the cap 41c. The sloped wall 45 may connect the inner wall 44a of the cap 41c to the outer wall 44b. The sloped wall 45 of the cap 41c may taper off its angle α to a horizontal or near-horizontal surface 45e as the sloped wall 45 meets the outer vertical wall 44b. The sloped wall 45 may also taper off its angle α to a vertical or near-vertical surface as the sloped wall 45 meets the inner wall 44a.

In one embodiment, the inner wall 44a has a diameter A of 0.281 inches, the outer wall 44b has a diameter B of 0.341 inches, the top lip 63c of the sensor post 59c has a diameter T of 0.265 inches, and the ring 60c has a diameter R in the range of 0.281 to 0.341 inches. In FIG. 9, P0 indicates a position at which the sloped wall 45 of the cap 41c makes initial contact with the ring 60c. P1 refers to a minimum position at which wall 45 is in contact with ring 60c and is still able to maintain a seal. Compared to P0, at position P1, the bottom-most point 45a of wall 45 is 0.003 inches below that of position P0. Position P1 may result when all valve actuators 56 of the valve and sensor assembly 54 (FIG. 5) are making impact onto the cassette 16, resulting in cassette deflection. Position P2 may result when fewer than all valve actuators 56 are making impact onto the cassette 16, resulting in less cassette deflection than when all valve actuators are making impact. Compared to P1, at position P2, the bottom-most point 45a of wall 45 is approximately 0.020 inches below that of position P1. Position P3 may be described as the nominal position of the cassette 16 when cassette deflection is at zero. Compared to P2, at position P3, the bottom-most point 45a of wall 45 is approximately 0.030 inches below that of position P2, and 0.053 inches below that of position P0.

Figure 10:
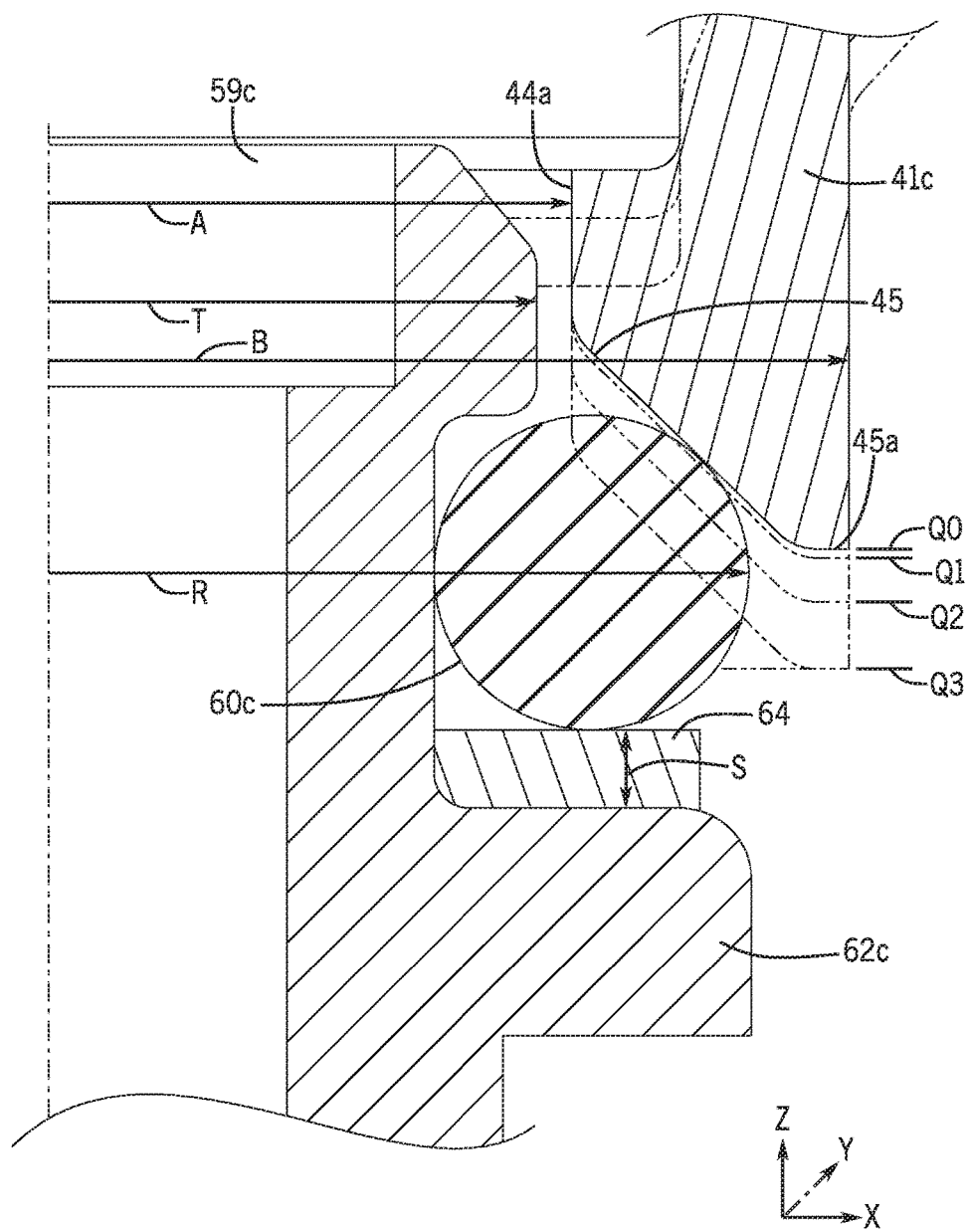
FIG. 10 is a cross-sectional diagram showing one side of a sensor post and shim fitted against a cap of a cassette sensing station at different compression levels, according to an exemplary embodiment.

FIG. 10 is a cross-sectional diagram showing one side of a sensor post 59c fitted against the cap 41c at different compression levels, according to an exemplary embodiment. In this embodiment, a shim 64 is inserted between the lower lip 62c and the ring 60c. The inner wall 44a may have a diameter A of 0.281 inches, the outer wall 44b may have a diameter B of 0.341 inches, the top lip 63c of the sensor post 59c may have a diameter T of 0.265 inches, and the ring 60c may have a diameter R of between 0.281 and 0.341 inches. The shim 64 may be inserted between the ring 60c and the bottom lip 62c to increase tolerance in the z-direction to account for cassette deflection during a fluid processing procedure. The shim 64 may have a height S in the range of 0.001 to 0.100 inches, preferably in the range of 0.010 to 0.030 inches, and more preferably approximately 0.020 inches, although any suitable shim height may be used. According to various embodiments, the shim may be compressible or non-compressible.

In FIG. 10, in one embodiment in which a shim 64 having a height S of 0.020 inches is implemented, position Q0 may comprise bottom-most point 45a of wall 45 resting 0.020 inches below position P0 of FIG. 9. Unlike at position P0, at position Q0, wall 45 may still sufficiently compress ring 60c to maintain an effective seal, due to the added height of 0.020 inches provided by the shim 64. Q1 refers to a new minimum position at which wall 45 is in contact with ring 60c and able to maintain a seal. Compared to Q0, at position Q1, the bottom-most point 45a of wall 45 is 0.003 inches below that of position Q0. Compared to P1, at position Q1, the bottom-most point 45a of wall 45 is 0.020 inches below that of position P1, due to the shim 64. Position Q1 may result when all valve actuators 56 of the valve and sensor assembly 54 are making impact onto the cassette 16, resulting in cassette deflection. Position Q2 may result when fewer than all valve actuators 56 are making impact onto the cassette 16, resulting in less cassette deflection than when all valve actuators are making impact. Compared to Q1, at position Q2, the bottom-most point 45a of wall 45 is approximately 0.020 inches below that of position Q1. Compared to P2, at position Q2, the bottom-most point 45a of wall 45 is 0.020 inches below that of position P2, due to the shim 64. Position Q3 may be described as the new nominal position of the cassette 16 when cassette deflection is at zero. At position Q3, the bottom-most point 45a of wall 45 is approximately 0.030 inches below that of position Q2, 0.053 inches below that of position Q0, 0.073 inches below that of P0, and 0.020 inches below that of P3.

In the embodiment in which a shim 64 of 0.020 inches is implemented, a compression of at least 0.005 inches may consistently be maintained at all times even when all valve actuators are making impact simultaneously, preferably a compression of greater than 0.020 inches, and more preferably a minimum compression of approximately 0.023 inches. In an embodiment in which inner wall 44a has a diameter A of 0.281 inches, top lip 63c of the sensor post 59c has a diameter T of 0.265 inches, and shim 64 has a height S of 0.020 inches, an effective seal may still be maintained when the cap 41c and sensor post 59c have shifted away from axis Zc (FIG. 8C) from each other in an x/y direction of up to 0.030 inches from their original concentric positions about axis Zc.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A fluid processing system comprising:
    a cassette comprising a molded body having a plurality of valve stations and at least one pressure sensing station, wherein the pressure sensing station comprises a cap having an opening extending beyond the molded body; and
    a loading area configured to receive and hold the cassette, and configured to position the cassette onto a valve and sensor assembly, wherein the valve and sensor assembly comprises valve actuators and at least one pressure sensing transducer comprising a sensor post, the valve and sensor assembly configured to align respectively with the plurality of valve stations and the pressure sensing station;

wherein the opening of the cap is formed by an inner wall having a first diameter, an outer wall having a second diameter, and a contact surface connecting the inner and outer wall, wherein the contact surface includes a varying diameter that decreases from the second diameter to the first diameter;

wherein the sensor post comprises a ring disposed around a cylindrical body and positioned to engage with the contact surface of the cap to form a seal; and wherein the contact surface is disposed at an acute angle relative to a vertical axis of the seal, the acute angle having a value in the range of 30 to 60 degrees.

2. The system of claim 1, wherein the pressure sensing transducer comprises at least one of a piezoelectric, bridge-based, capacitive, and optical mechanism.

3. The system of claim 1, wherein the sensor post further comprises a bottom lip configured to contact and support the ring.

4. The system of claim 1, wherein the sensor post further comprises a top lip having a diameter greater than a diameter of the cylindrical body.

5. The system of claim 4, wherein the ring is compressed between the contact surface and the sensor post.

6. The system of claim 1, wherein the ring comprises at least one of silicone, nitrile rubber, and a fluoropolymer elastomer, and comprises a hardness value in the range of 20 to 100 durometers.

7. The system of claim 1, wherein the ring is configured to exert a force against the cap at an acute angle relative to a vertical axis of the seal.

8. A fluid processing cassette and sensor coupling system comprising:

a cassette comprising a cap having an opening formed by an inner cylindrical wall having a first diameter, an outer cylindrical wall having a second diameter, and a contact surface connecting the inner and outer cylindrical walls, wherein the contact surface includes a varying diameter that decreases from the second diameter to the first diameter; and a sensor post comprising a ring disposed around a cylindrical body and positioned to engage with the contact surface of the cap to form a seal, wherein the contact surface is disposed at an acute angle relative to a vertical axis of the seal, the acute angle having a value in the range of 30-60 degrees.

9. The system of claim 8, wherein the sensor post further comprises a bottom lip configured to contact and support the ring.

10. The system of claim 8, wherein the sensor post further comprises a top lip having a diameter greater than a diameter of the cylindrical body.

11. The system of claim 10, wherein the ring is compressed between the contact surface and the sensor post.

12. The system of claim 8, wherein the ring comprises at least one of silicone, nitrile rubber, and a fluoropolymer elastomer, and comprises a hardness value in the range of 20 to 100 durometers.

13. The system of claim 8, wherein the ring is configured to exert a force against the cap at an acute angle relative to a vertical axis of the seal.

* * * * *